United States Patent
Lassen et al.

(10) Patent No.: US 6,521,811 B1
(45) Date of Patent: *Feb. 18, 2003

(54) ABSORBENT ARTICLE HAVING A BODY-ACCOMMODATING ABSORBENT CORE

(75) Inventors: Frederich Oma Lassen, Neenah, WI (US); Jane Marilyn Anton, Neenah, WI (US); Linda Jean Chmielewski-Larsen, Bloomington, IL (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/668,725

(22) Filed: Sep. 22, 2000

Related U.S. Application Data

(63) Continuation of application No. 08/733,090, filed on Oct. 16, 1997, now Pat. No. 6,160,197, which is a continuation of application No. 08/259,221, filed on Jun. 13, 1994, now abandoned.

(51) Int. Cl.[7] ............................ A61F 13/15; A61F 13/20
(52) U.S. Cl. .................... 604/378; 604/380; 604/385.01
(58) Field of Search ................. 604/358, 365, 604/367, 374, 377, 378, 379, 380, 385.01, 382, 385.03, 385.101

(56) References Cited

U.S. PATENT DOCUMENTS

| | | |
|---|---|---|
| 75,036 A | 3/1868 | Manheim |
| 810,131 A | 1/1906 | Green |
| 810,132 A | 1/1906 | Green |
| 2,064,431 A | 12/1936 | Jurgensen |
| 2,331,355 A | 10/1943 | Strongson |
| 2,662,527 A | 12/1953 | Jacks |
| 2,747,575 A | 5/1956 | Mercer |
| 2,787,271 A | 4/1957 | Clark |
| 2,952,260 A | 9/1960 | Burgeni |
| 3,211,147 A | 10/1965 | Pherson et al. |

(List continued on next page.)

FOREIGN PATENT DOCUMENTS

| | | | |
|---|---|---|---|
| AU | A-43706/89 | 4/1990 | ........... A61F/13/18 |
| DE | 1 435 861 | 2/1969 | |
| DE | 35 08 280 A1 | 9/1986 | ........... A61F/13/16 |
| EP | 0 136 524 A1 | 4/1985 | ........... A61F/13/18 |
| EP | 0 162 451 A1 | 11/1985 | ........... A61F/13/16 |
| EP | 0 613 671 A2 | 9/1994 | ........... A61F/13/15 |
| GB | 2 124 499 A | 2/1984 | ........... A61F/13/16 |
| GB | 2 258 403 A | 2/1993 | ........... A61F/13/15 |
| WO | WO 09/04374 | 5/1990 | ........... A61F/13/16 |
| WO | WO 92/10984 | 7/1992 | ........... A61F/13/15 |
| WO | WO 94/05244 | 3/1994 | ........... A61F/13/46 |
| WO | WO 95/07674 | 3/1995 | ........... A61F/13/15 |

*Primary Examiner*—Glenn K. Dawson
*Assistant Examiner*—Michele Kidwell
(74) *Attorney, Agent, or Firm*—Wilhelm Law Service; Thomas D. Wilhelm

(57) ABSTRACT

An absorbent article for absorbing body fluids is provided having an absorbent core positioned between a fluid-permeable cover and a fluid-impermeable baffle. The absorbent core includes a central, longitudinal flexure axis which substantially extends the length of the absorbent core. The central, longitudinal axis generally divides the absorbent core into first and second longitudinal members having an outer boundary and wherein the first member has a second flexure axis and the second member has a third flexure axis. Flanking the outer boundary of the first and second members are a third and a fourth longitudinal absorbent members, respectively. The third and fourth absorbent members are positioned so that, when said absorbent article is subjected to lateral compressive forces, the first and second members preferentially bend convexly upward, and said absorbent core generally acquires a "W" shaped configuration.

21 Claims, 6 Drawing Sheets

U.S. PATENT DOCUMENTS

| | | |
|---|---|---|
| 3,343,543 A | 9/1967 | Glassman |
| 3,411,504 A | 11/1968 | Glassman |
| 3,525,337 A | 8/1970 | Simons et al. |
| 3,575,174 A | 4/1971 | Mogor |
| 3,805,790 A | 4/1974 | Kaczmarzyk et al. |
| 3,954,107 A | 5/1976 | Chesky et al. |
| 4,029,101 A | 6/1977 | Chesky et al. |
| 4,067,336 A | 1/1978 | Johnson |
| 4,182,334 A | 1/1980 | Johnson |
| 4,340,058 A | 7/1982 | Pierce et al. |
| 4,389,211 A | 6/1983 | Lenaghan |
| 4,568,341 A | 2/1986 | Mitchell et al. |
| 4,576,596 A | 3/1986 | Jackson et al. |
| 4,578,070 A | 3/1986 | Hoitman |
| 4,627,848 A | 12/1986 | Lassen et al. |
| 4,631,062 A | 12/1986 | Lassen et al. |
| 4,636,209 A | 1/1987 | Lassen |
| 4,655,759 A | 4/1987 | Romans-Hess et al. |
| 4,666,440 A | 5/1987 | Malfitano |
| 4,673,403 A | 6/1987 | Lassen et al. |
| 4,676,784 A | 6/1987 | Erdman et al. |
| 4,685,914 A | 8/1987 | Holtman |
| 4,701,177 A | 10/1987 | Ellis et al. |
| 4,743,245 A | 5/1988 | Lassen et al. |
| 4,753,644 A | 6/1988 | Cottenden et al. |
| 4,758,240 A | 7/1988 | Glassman |
| 4,795,453 A | 1/1989 | Wolfe |
| 4,804,380 A * | 2/1989 | Lassen .................... 604/385.1 |
| 4,840,692 A | 6/1989 | Kamstrup-Larsen |
| 4,846,824 A | 7/1989 | Lassen et al. |
| 4,935,021 A | 6/1990 | Huffman et al. |
| RE33,351 E | 9/1990 | Papajohn |
| 5,053,029 A | 10/1991 | Yang |
| 5,151,091 A | 9/1992 | Glaug et al. |
| 5,171,302 A | 12/1992 | Buell |
| 5,197,959 A | 3/1993 | Buell |
| 5,211,641 A | 5/1993 | Roos et al. |
| 5,300,055 A * | 4/1994 | Buell ...................... 604/385.1 |
| 5,312,386 A | 5/1994 | Correa et al. |
| 5,342,337 A | 8/1994 | Runeman et al. |
| 5,961,505 A | 10/1999 | Coe et al. |

* cited by examiner

ABSORBENT ARTICLE HAVING A BODY-ACCOMMODATING ABSORBENT CORE

CROSS-REFERENCE TO RELATED APPLICATIONS

This application is a Continuation application claiming priority under 35 U.S.C. 120 to application Ser. No. 08/733,090 filed Oct. 16, 1996 now U.S. Pat. No. 6,160,197, which is a Continuation application of abandoned application Ser. No. 08/259,221 filed Jun. 13, 1994 now abandoned, both of which are incorporated herein by reference in their entireties.

FIELD OF THE INVENTION

The present invention relates to disposable absorbent articles and, more particularly, to absorbent articles having a central, longitudinal flexure axis which allows the absorbent article to preferentially bend in an upwardly convex configuration when subjected to lateral compressive forces.

BACKGROUND OF THE INVENTION

All manner and variety of absorbent articles configured for absorption of body fluids, such as menses, urine, and feces, are well known. In the area of external feminine protection, for a sanitary napkin to receive menses, the sanitary napkin generally forms both a longitudinal and an arcuate configuration due to the contour of the wearer's body within the area of the vulva, perineum, and buttocks. Accordingly, it has been relatively difficult to obtain a proper fit of such sanitary napkin which would provide comfort to the wearer and prevent leakage at the edges thereof. Typically, in order for the sanitary napkin to have adequate fluid capacity and sufficient area to fully underlie the vulva, the sanitary napkin must have a width of such extent that it quickly becomes laterally compressed between the wearer's legs. As a result, the sanitary napkin rapidly deforms into a shapeless condition which causes it to fail. Some efforts at improving the construction of the sanitary napkin have been made, but they are still found to be inadequate at intercepting body fluids.

SUMMARY OF THE INVENTION

Briefly, this invention relates to disposable absorbent articles having a liquid-permeable cover, a liquid-impermeable baffle and an absorbent core for absorbing body fluid exudates. The absorbent core includes a central, longitudinal flexure axis which substantially extends the length of the absorbent core. The central, flexure axis at least partially divides the absorbent core into first and second members. The first member includes a second longitudinal flexure axis, and the second member includes a third longitudinal flexure axis. The central, longitudinal flexure axis allows the absorbent core to preferentially bend upwardly toward the cover and along the central, flexure axis in a convex configuration when the absorbent core is subjected to lateral compressive forces. This allows the absorbent core to substantially form an inverted "V" shape.

In a preferred embodiment, the absorbent core includes third and fourth longitudinal absorbent members flanking the first and second members respectively. This allows the absorbent article to acquire a more defined "W" shaped configuration when lateral compressive forces are applied to the absorbent article.

It is a general object of the invention to provide an absorbent article that is inherently self-adjusting and form-fitting to the body and which permits compression of the pad without destroying the basic shape thereof. A more specific object of the invention is to provide an absorbent core that will preferentially bend upwardly, in a convex configuration, when subjected to lateral compressive forces, substantially forming an inverted "V" shape in the central region of the core.

A further object of this invention is to provide a sanitary napkin having a body surface that is generally "W" shaped in the central region when being worn.

Another object of this invention is to provide a sanitary napkin that will adapt its shape so as to conform to the changing shape of the vulva region of a woman whether the wearer is stationary or in motion.

Still another object of this invention is to provide a sanitary napkin having multiple, longitudinal absorbent members that preferentially bend upwardly toward the cover in a convex configuration when subjected to lateral compressive forces.

Other objects and advantages of the present invention will become more apparent to those skilled in the art in view of the following description and the accompanying drawings.

BRIEF DESCRIPTION OF THE DRAWINGS

It is believed the invention will be better understood from the following description taken in conjunction with the accompanying drawings, wherein like numerals of reference indicate the same parts throughout the several views, and analogous parts are designated with a prime symbol.

DETAILED DESCRIPTION OF THE PREFERRED EMBODIMENTS

Figure 1:
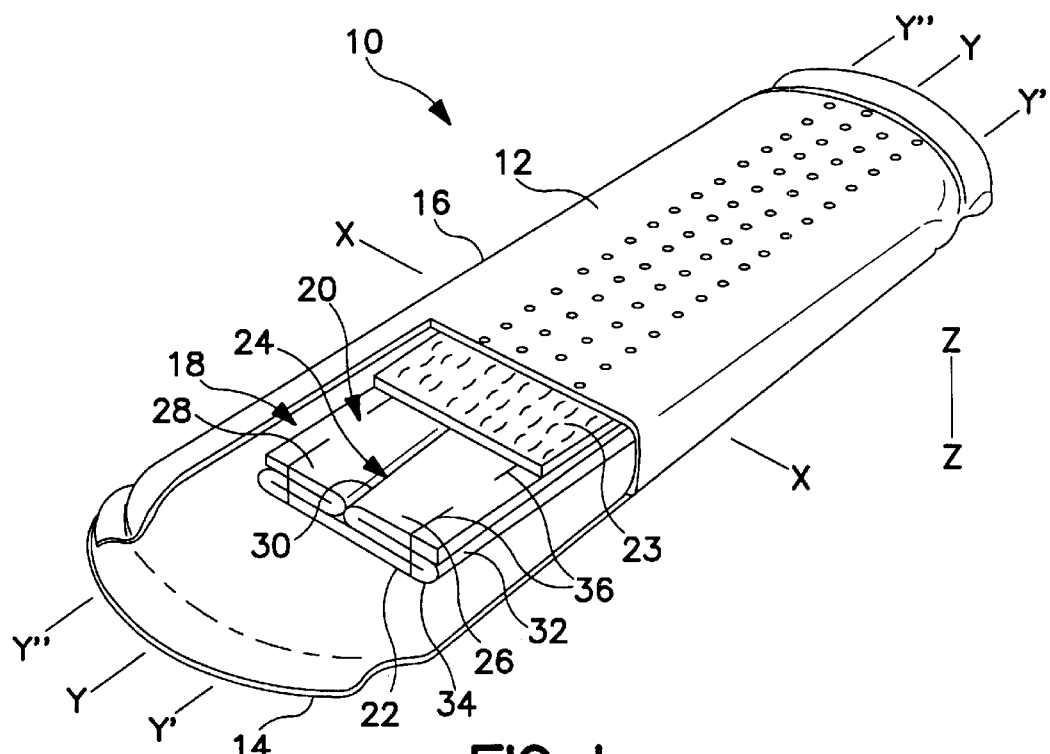
FIG. 1 is a partial cut-away perspective view of an absorbent article illustrating an embodiment of the absorbent core of the present invention with the central, longitudinal flexure axis substantially dividing the absorbent core into a first and a second member.

Referring to FIG. 1, an absorbent article 10 is shown for absorbing human body fluids. For convenience of description only, the absorbent article 10 is illustrated as a sanitary napkin for feminine hygiene having generally a race-track shape. However, it can be a panty shield, an incontinence device, or any other disposable absorbent article that is well known in the art, and can include other shapes, such as oval, hourglass, straight sided, wrapped and peripheral sealed constructions. It should be noted that panty liners, feminine pads, and incontinence garments come in various sizes and shapes and vary in thickness.

The sanitary napkin 10 includes a liquid-pervious cover 12, a liquid-impervious baffle 14, an outer periphery 16, and an absorbent core 18 located intermediate the cover 12 and the baffle 14. The absorbent core 18 is positioned inward from the outer periphery 16 of the sanitary napkin 10 and includes a body-facing surface 20 positioned adjacent the cover 12 and a garment-facing surface 22 positioned adjacent the baffle 14. Optionally, the sanitary napkin 10 can include a transfer layer 23 positioned between the cover 12 and the absorbent core 18 for rapidly transporting body fluids into the absorbent core 18 and to reduce the occurrence of rewet.

Describing the individual elements in greater detail, the cover 12 is oriented towards and contacts the body of the wearer and receives bodily discharges. The cover 12 is liquid pervious and should be flexible and non-irritating to the skin. As used herein, the term "flexible" refers to materials which are compliant and readily conform to the shape of the body or respond by easily deforming in the presence of external forces.

The cover 12 can surround the absorbent core 18 so that it completely encases the sanitary napkin 10. Alternatively, the cover 12 and the baffle 14 can extend beyond the absorbent core 18 and be peripherally joined together using known techniques either entirely, so that the entire outer periphery 16 of the sanitary napkin 10 is circumscribed by their joinder, or the cover 12 and baffle 14 can be partially peripherally joined. Typically, the cover 12 and the baffle 14 can be joined by a construction adhesive, by ultrasonic bonding, or any other joining method known in the art.

The liquid-permeable cover 12 should be sanitary, clean in appearance, and somewhat opaque to hide bodily discharges collected in and absorbed by the absorbent core 18. The cover 12 should further exhibit good strike-through and rewet characteristics permitting bodily discharges to rapidly penetrate through the cover 12 to the absorbent core 18 but not allow the body fluid to flow back through the cover 12 to the skin of the wearer. Any material meeting the above criteria is suitable for use as a cover. For example, suitable materials for the cover 12 can be nonwoven materials, perforated thermoplastic films, or combinations thereof. A nonwoven fabric made from polyester, polyethylene, polypropylene, bicomponent, nylon, rayon, or like fibers can be used. The cover 12 can contain a plurality of apertures formed therethrough to permit body fluid deposited thereon to pass through into the absorbent core 18.

If desired, the cover 12 may be sprayed with a surfactant to enhance liquid penetration to the absorbent core 18. The surfactant is typically non-ionic and should be non-irritating to the skin.

The transfer layer 23 preferably is comprised of a fibrous blend of polyester, rayon and a polymeric fiber such as that marketed by C. Itoh & Co. under the tradename "CHISSO". A highly preferred composition is comprised of 50 percent polyester fibers with a length of approximately 3 to about 6 millimeters, approximately 30 percent straight rayon fibers with a fiber length of about 5 to about 10 millimeters, and the balance CHISSO with a fiber length also about 5 to about 10 millimeters. Other compositions will occur to those of ordinary skill in the art and may be substituted with due consideration for the functional requirements of a transfer layer, i.e., rapid wicking of fluid downward in the Z-direction. It is important to the functionality of the absorbent core 18 that it have the mobility to assume various body-accommodating configurations. Therefore, the transfer layer 23, or any other material, if employed, that would reside between the cover 12 and the absorbent core 18, is secured in such a manner that would not impede this functionality. Accordingly, the transfer layer 23 should allow the absorbent core 18 to bend convexly, to form an inverted "V", when lateral compressional forces are exerted on it.

The liquid-impermeable baffle 14 may be any desired material that is flexible and prevents the intercepted body fluid from soiling the clothing of the wearer. Any material used in the prior art for such purposes can be utilized herein. Suitable materials include embossed and nonembossed thermoplastic films and laminated tissue. A preferred material is a polyethylene film.

The absorbent core 18 is interposed between the cover 12 and the baffle 14. This construction prevents the absorbent material from shredding or becoming detached while the sanitary napkin 10 is worn and also ensures proper containment of bodily discharges. This arrangement also helps provide for a unitary assembly of the sanitary napkin 10. Any joined arrangement that provides for the capture of the absorbent core 18 intermediate the cover 12 and the baffle 14 and a unitary assembly is suitable. The absorbent core 18 serves to collect and retain bodily discharges, particularly menses and blood, deposited thereon or which otherwise transverses through the liquid-permeable cover 12.

The absorbent core 18 can be any absorbent material which is generally conformable, non-irritating to the wearer's skin and capable of absorbing and containing liquids and certain body exudates. The absorbent core 18 may be utilized in a wide variety of sizes and shapes of absorbent articles, such as rectangular, hourglass or racetrack to name a few. The absorbent core 18 can be constructed of comminuted wood pulp, creped cellulose wadding, absorbent foams, absorbent sponges, superabsorbent polymers, absorbent hydrogel materials, polymeric fibers, or any equivalent materials or combinations of materials. Preferably, the absorbent core 18 is a meltblown tissue of one or more layers. Each layer can have a basis weight of about 30 grams to about 100 grams per square meter (gsm) and made in accordance with U.S. Pat. No. 4,798,603 issued to Meyer and assigned to Kimberly-Clark Corporation, the entire disclosure of which is incorporated herein by reference and made a part hereof. The total absorbent capacity of the absorbent core 18 should, however, be compatible with the design exudate loading for the intended use of the sanitary napkin 10. Further, the size may be varied to accommodate a predetermined expected amount of exudate fluid volume. For instance, a different absorbent capacity may be utilized for sanitary napkins intended for nighttime use, or for sanitary napkins intended for use by teenagers, as compared with those intended for use by more mature women.

Generally, the sanitary napkin 10 and absorbent core 18 have a common longitudinal centerline Y-Y. The absorbent core 18, as illustrated in FIG. 1, is constructed of a meltblown tissue that has approximately two-thirds of the tissue bi-folded to form left and right halves of the absorbent core 18. Positioned along the longitudinal centerline Y-Y, and substantially extending the length of the absorbent core 18, is an axis 24, also referred to herein as a central longitudinal flexural axis, a central longitudinal axis, a central flexure axis, and a longitudinal flexure axis. The central, longitudinal flexure axis 24 can be positioned transversely, i.e., along the X-X axis, and off center from the longitudinal center line Y-Y, a distance ranging from about 0 to about 10 millimeters, without adversely effecting the functionality of the absorbent core 18 to adopt various body-accommodating configurations. Preferably, the central, longitudinal flexure axis 24 is aligned along the longitudinal center line Y-Y thereby dividing the absorbent core 18 into two substantially symmetrical opposite halves. The central, longitudinal flexure axis 24 can extend longitudinally from about 50 to about 100 percent of the length of the absorbent core 18 and, advantageously, will extend from about 75 to 100 percent of the length of the absorbent core 18.

As illustrated in FIG. 1, the central, flexure axis 24 divides the absorbent core 18 into a first member 26 and a second member 28 which corresponds to the right and left halves of the absorbent core 18. The central, longitudinal flexure axis 24 provides a means for directing fluid flow downward in the Z-direction and into the absorbent core 18. The central, longitudinal flexure axis also directs body fluids longitudinally, along the length of the absorbent core 18, reducing the likelihood of body fluid transversely crossing, i.e., along the X-X direction, of the sanitary napkin 10. Thus, there is less likelihood of body fluids causing a side failure and there is a greater utilization of absorbent capacity.

The central, longitudinal axis 24 can have a slit or a channel 30 having a "V" or "U" shape. The slit or channel 30 extends through about 3 to about 99 percent of the thickness of the absorbent core 18, more preferably through about 40 to about 95 percent of the thickness of the absorbent core 18, and most preferably through at least about 80 percent of the thickness of the absorbent core 18. Advantageously, the slit or channel 30 forms a pocket or well in the Z-direction for receiving body fluids. This configuration allows for rapid absorption of the body fluid without the usual impairment encountered when the fluid-receiving surface located adjacent to the wearer's skin is flat or cup shaped (concave).

The channel 30 should not extend completely through the absorbent core 18. It has been discovered that such a configuration allows for the absorbent core 18 to unpredictably and undesirably form a "V" shape, unless other means are employed to ensure that the absorbent will form an inverted "V" shape.

It is important to the functionality of this invention that the absorbent core 18 be attached to the baffle 14 by means which permits the absorbent core 18 to bend upward along the central, longitudinal flexure axis 24 when lateral compressional forces are applied to the absorbent core 18. Such attachment means includes using ultrasonics to intermittently point bond the absorbent core 18 to the baffle 14 and/or cover 12, or applying a thin layer or intermittent layer or pattern of construction adhesive. Suitable adhesives can be of the type well known in the disposable absorbent article art. Other means for securing the absorbent core 18 are equally acceptable provided that the securement does not interfere with the ability of central, longitudinal flexure axis 24 to preferentially bend upward to form a convex configuration.

The central, longitudinal flexure axis 24 at least partially divides the absorbent core 18 into a first member 26 and a second member 28. Since the members 26 and 28 are similar in their construction, only one will be described. The first member 26 has a longitudinal outer boundary 32 and spaced-apart transverse ends 34, only one of which is shown. The outer boundary 32 and the transverse end 34 partially define the outer perimeter of the absorbent core 18. The first member 26 includes a second flexure axis Y'-Y' located laterally adjacent to the central, longitudinal flexure axis 24. During use, the second flexure axis Y'-Y' allows lateral torsional forces to be distributed longitudinally across the central, longitudinal flexure axis 24. Without the second flexure axis Y'-Y', these forces may otherwise contort the central, longitudinal flexure axis 24 into an undesired configuration. The central, longitudinal flexure axis 24, in combination with the second and third flexure axes Y'-Y' and Y"-Y", respectively, allows the absorbent core 18 to preferentially bend upward along the flexure axis 24 and toward the cover 12 in a convex configuration when the sanitary napkin 10 is subjected to lateral compressive forces. The first member 26 and the second member 28 of the absorbent core 18 are permitted to separate from each other causing the absorbent core 18 to substantially acquire an inverted "V" shape. Also, by longitudinally distributing the torsional forces, the absorbent core 18 will generally accommodate various body geometries and adapt to the wearer. It will also be recognized that, if the absorbent core 18 is sufficiently compressed, the second and third flexure axes Y'-Y' and Y"-Y" can allow the absorbent core 18 to bend along these axes to acquire a "W" shape. Preferably, the second flexure axis Y'-Y' is spaced a distance between about 5 millimeters to about 25 millimeters from the central, longitudinal flexure axis 24. The second flexure axis Y'-Y' can have one or more slits 36, voids (such as apertures substantially along the Y'-Y' axis), internal shaped components, interfaces, gaps, and the like. It is important to this invention that the second flexure axis Y'-Y' allow fluid communication on either side of the axis. By "fluid communication," we mean that the second flexure axis Y'-Y' does not significantly impede the transverse (in the X-X direction) transfer/migration of body fluid across the absorbent core 18. This, too, permits a greater utilization of the absorbent capacity of the sanitary napkin 10.

The slits 36 extend through at least about 75 percent of the thickness of the first member 26. Advantageously, the slits 36 extend through about 90 percent of the thickness and, optimally, 100 percent. As used herein, the term "thickness" means the distance occupied by the absorbent material as measured in the Z-direction. The slits 36 do not extend through the baffle 14. Each slit 36 is longitudinally spaced apart from an adjacent slit 36 by a distance of about 5 millimeters to about 35 millimeters and, preferably, from about 10 millimeters to about 30 millimeters. During use, the slits 36 function cooperatively to advantageously produce areas of stress relief on the first member 26.

Figure 2:
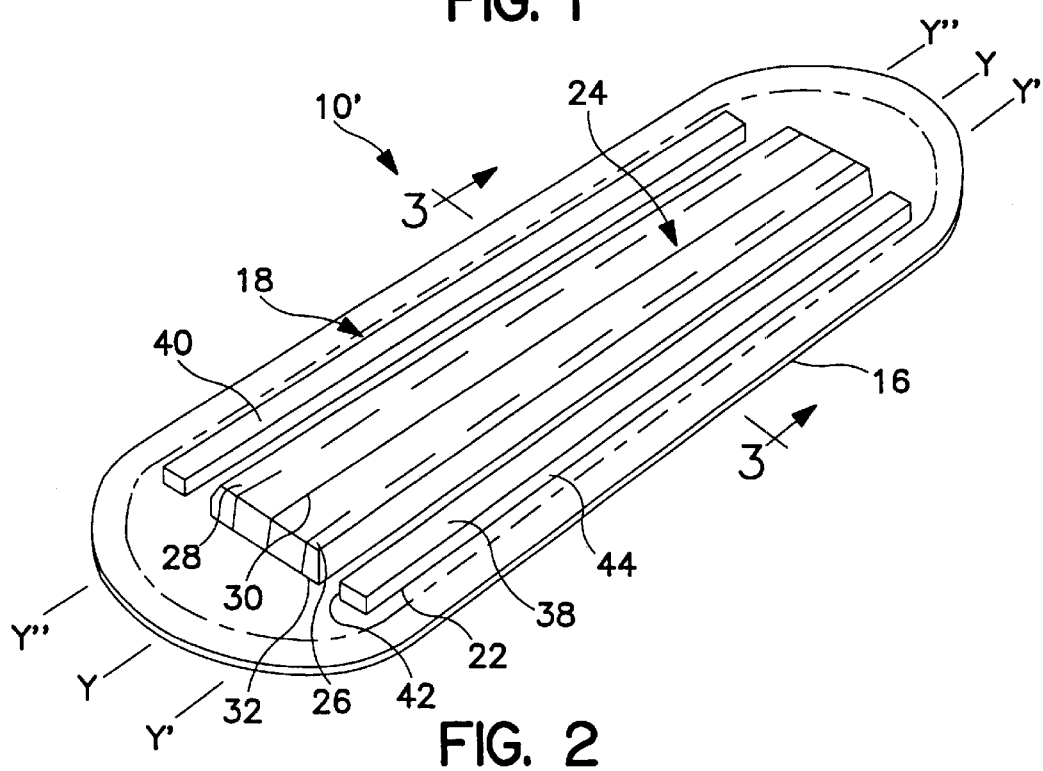
FIG. 2 is a perspective view of another embodiment of an absorbent article with the cover removed and showing an absorbent core having third and fourth members flanking the sides of the first and second members.
Figure 3:
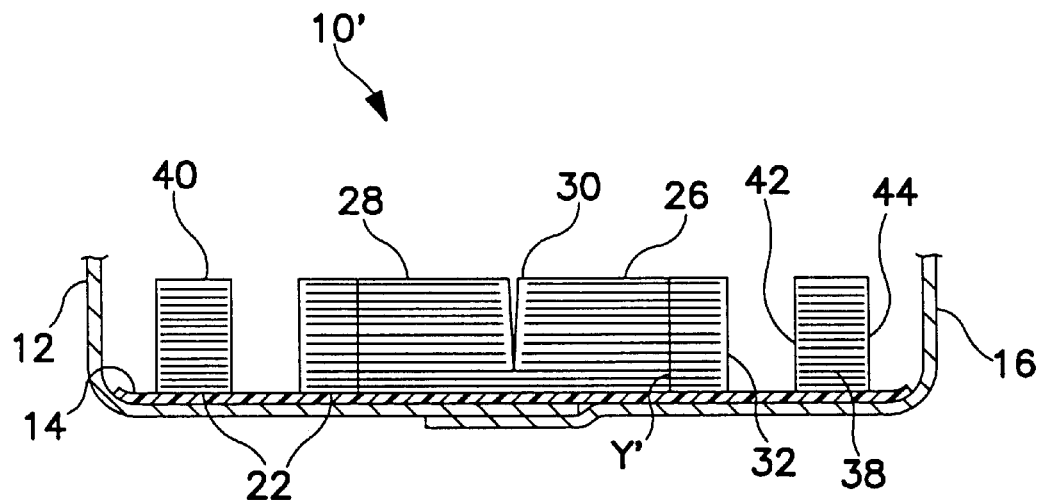
FIG. 3 is a cross-sectional view taken along line 3—3 of FIG. 2.

Referring to FIG. 2, another embodiment of the sanitary napkin 10' is shown but without a cover. In this embodiment, the absorbent core 18 includes the addition of a third and a fourth longitudinal absorbent member 38 and 40 located adjacent to the first and second members 26 and 28, respectively. The first and second members 26 and 28 are similar to those described above. For purposes of describing the invention, only the third longitudinal absorbent member 38 will be further described. The third longitudinal absorbent member 38 has a predetermined thickness which can be less than, equal to, or greater than, the thickness of the first member 26. The thickness of the third longitudinal absorbent member 38 can range from about 2 millimeters to about 20 millimeters. The third longitudinal absorbent member 38 has an inner longitudinal surface 42 and an outer longitudinal surface 44. The inner surface 42 is positioned laterally adjacent to, but spaced from, the outer boundary 32 of the first member 26. The inner surface 42 of the third member 38 can be spaced apart from the outer boundary 32 of the first member 26 by a distance ranging from about 3 millimeters to about 25 millimeters at rest, as illustrated in FIG. 3. Preferably, the inner surface 42 is spaced from the outer boundary 32 by a distance which is substantially equal to the predetermined thickness of the third longitudinal absorbent member 38. This allows the inner surface 42 of the absorbent member 38 to properly contact the outer boundary 32 of the first member 26, permitting the sanitary napkin 10' to adopt various configurations in response to lateral compressional forces typically exerted on the sanitary napkin 10' during use.

The outer surface 44 is positioned adjacent to the outer periphery 16 of the sanitary napkin 10'. The longitudinal outer surface 44 can be positioned inward from the sanitary napkin's outer periphery 16 a distance of about 1 millimeter to about 25 millimeters and, more preferably, from about 5 millimeters to about 20 millimeters. This distance reduces or prevents the chance that body fluid not absorbed into the absorbent core 18 will migrate to the outer periphery 16 of the sanitary napkin 10' and possibly contribute to a failure of the sanitary napkin 10' to capture and retain the body fluid.

Figure 4:
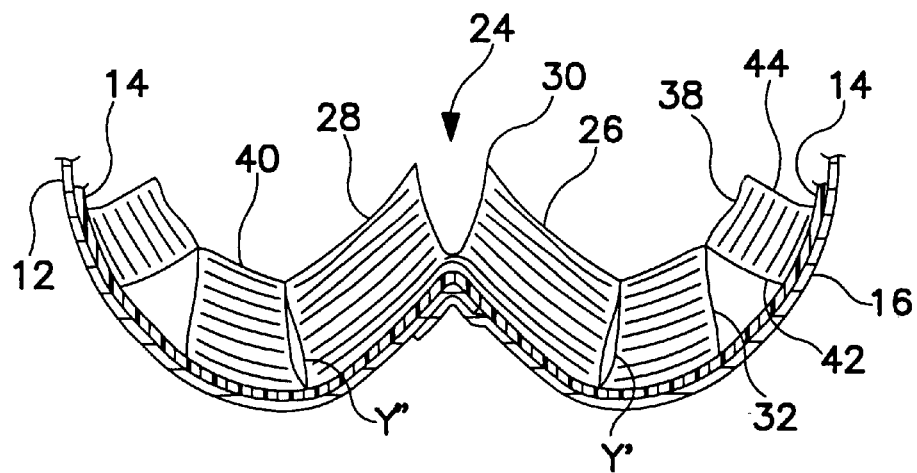
FIG. 4 is a view of FIG. 3 illustrating a "W" configuration which the absorbent core can adopt when lateral, compressional forces are exerted on the absorbent core.

Referring to FIGS. 3 through 8, during use, when the sanitary napkin 10' is subjected to the lateral compressive forces, the sanitary napkin 10' and the central, longitudinal flexure axis 24 can assume a number of different configurations ranging from an at-rest configuration, shown by FIG. 3, to an in-use "W" configuration, shown by FIG. 4. Generally, FIGS. 5 through 8 depict the most common shapes the sanitary napkin 10' will assume in conforming to the wearer's anatomy. The sanitary napkin 10' can be divided into three substantially equal regions:

1) an anterior region 60;
2) a posterior region 62; and
3) a central region 64 positioned therebetween.

In FIGS. 5 through 8, the anterior region 60 is that area of the sanitary napkin 10' that would face forward when positioned in a wearer's undergarment. In these figures, the anterior region 60 is generally located outside the area subject to direct compressional forces, such as those exerted on the sanitary napkin 10' by the thighs during use, so that it retains a substantially circular shape. During use, the anterior region 60 can also acquire a slightly upwards, toward-the-body, open cup shape. However, the shape of the posterior region 62 and the central region 64 of the sanitary napkin 10' are greatly affected by a woman's anatomical geometries. FIGS. 2, and 5 through 8, illustrate the ability of the absorbent core 18 of this invention to conform to a variety of body shapes during rest and during activities.

Figure 5:
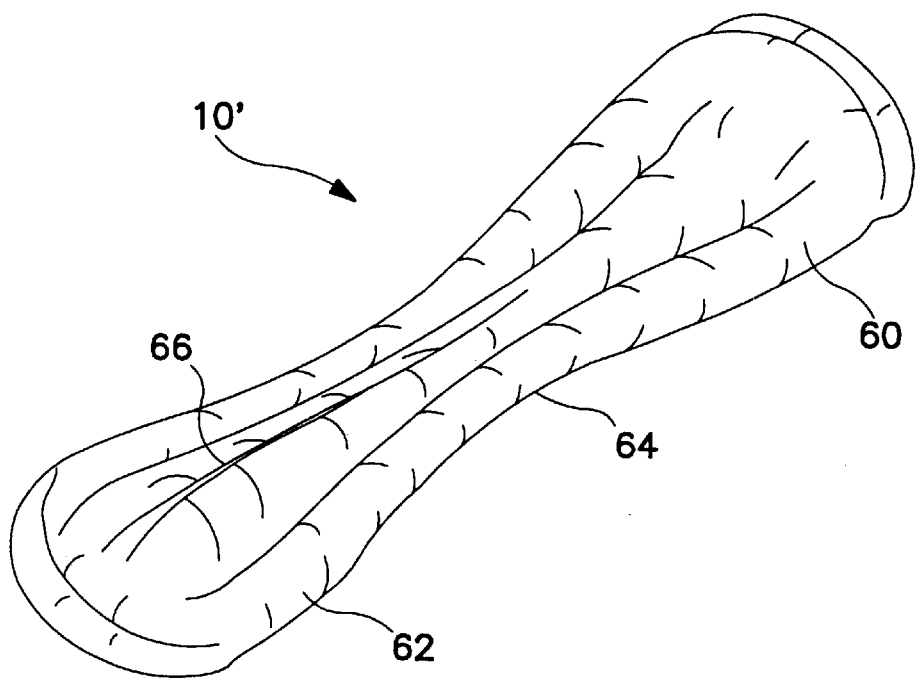
FIG. 5 is a perspective view of an absorbent article showing generally a body-accommodating configuration, referred to herein as a "W" shape, the absorbent core can obtain when lateral compressional forces are exerted on the absorbent core.

Referring to FIGS. 2, 4, and 5, the absorbent core 18 allows the sanitary napkin 10' to assume a configuration generally known by those skilled in the art as a "W" configuration. In this configuration, the posterior region 62 of the sanitary napkin adapts to the gluteal groove of the wearer by bending, as viewed from the central region 64 to the posterior region 62, along the central, longitudinal flexure axis 24 upward toward the body of the wearer. The upward curvature of the absorbent core 18 forms an inverted "V" configuration having an apex 66. The apex 66 of the convexly shaped body surface remains the apex 66 into the posterior region 62. Since the sanitary napkin 10' in all probability will be worn in a wearer's undergarment, the upwardly acting forces of the undergarment preferably will cause the posterior region 62 and the rearward part of the central region 64 to curve upwards toward the wearer's body and follow the curve of the buttocks. The apex 66 of the posterior region adapts to fit the gluteal groove of the wearer when worn. The apex 66 is, generally, symmetrically located between the outer periphery 16 of the sanitary napkin 10' and along the longitudinal center line Y-Y. The apex 66 fits the gluteal groove of the buttocks to provide stability against sideways shifting of the sanitary napkin 10'.

The central region 64 adopts a shape that is best illustrated in FIG. 4. When the sanitary napkin 10' is subjected to lateral compressive forces, such as those when the sanitary napkin is being worn, the cover 12 and the absorbent core 18 generally bend in cooperation along the longitudinal flexure axis 24 into a convex upward configuration. The inner longitudinal surface 42 of the third and fourth longitudinal absorbent members 38 and 40 remain adjacent to the outer boundary 32 of the first and second member 26 and 28, respectively, thereby transferring the lateral compressive forces along the length of the second and third flexure axis Y'-Y' and Y"-Y" to the central, longitudinal flexure axis 24. The outer longitudinal surface 44 of the third and fourth absorbent members 38 and 40 advantageously moves upward to form a barrier that assists in preventing the absorbed body fluid from escaping the sanitary napkin 10' via the outer periphery 16. Thus, the sanitary napkin 10' generally assumes a "W" shaped cross-section in the central region 64.

Figure 6:
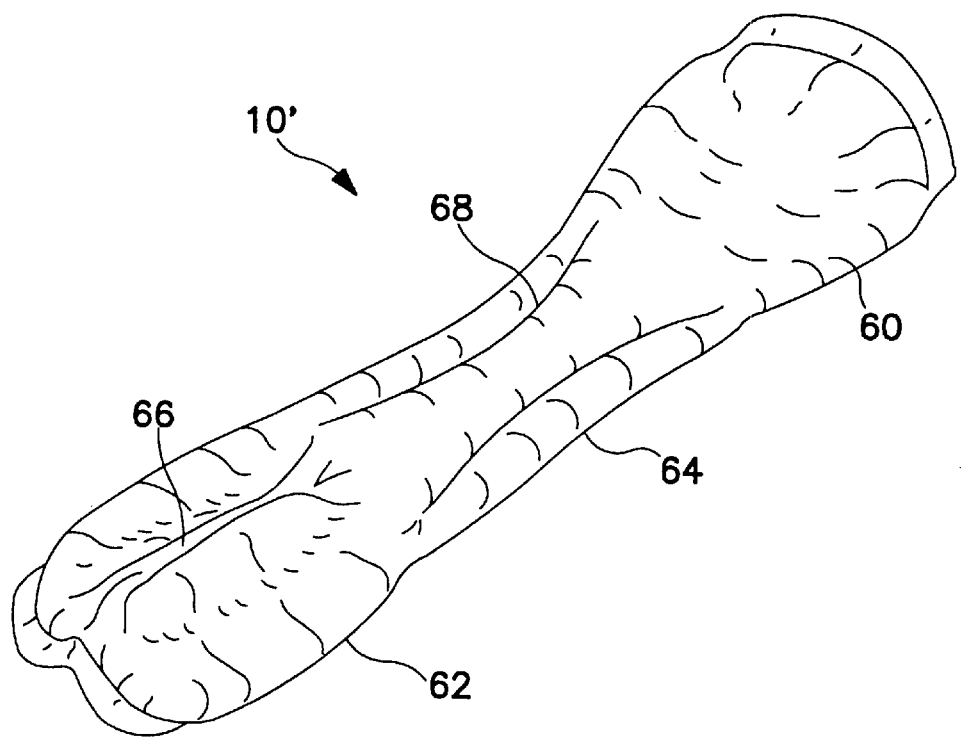
FIG. 6 is a perspective view of an absorbent article showing another body-accommodating configuration, referred to herein as the "panty liner" shape, the absorbent core can obtain when lateral compressional forces are exerted on the absorbent core.

Referring to FIGS. 2 and 6, the absorbent core 18 allows the sanitary napkin 10' to assume another configuration described herein as a "panty liner" configuration. In this configuration, the posterior region 62 of the sanitary napkin 10' is similar to that described above for the posterior region 62 of the "W" shape. However, the central region 64 adopts a configuration wherein the first and second absorbent members 26 and 28 remain in face-to-face contact with each other and do not bend upwardly along the longitudinal axis Y-Y. The inner longitudinal surface 42 of each third and fourth absorbent members 38 and 40 moves inward toward the longitudinal outer boundary 32 of each first and second members 26 and 28 to form a well 68 through the central region 64.

Figure 7:
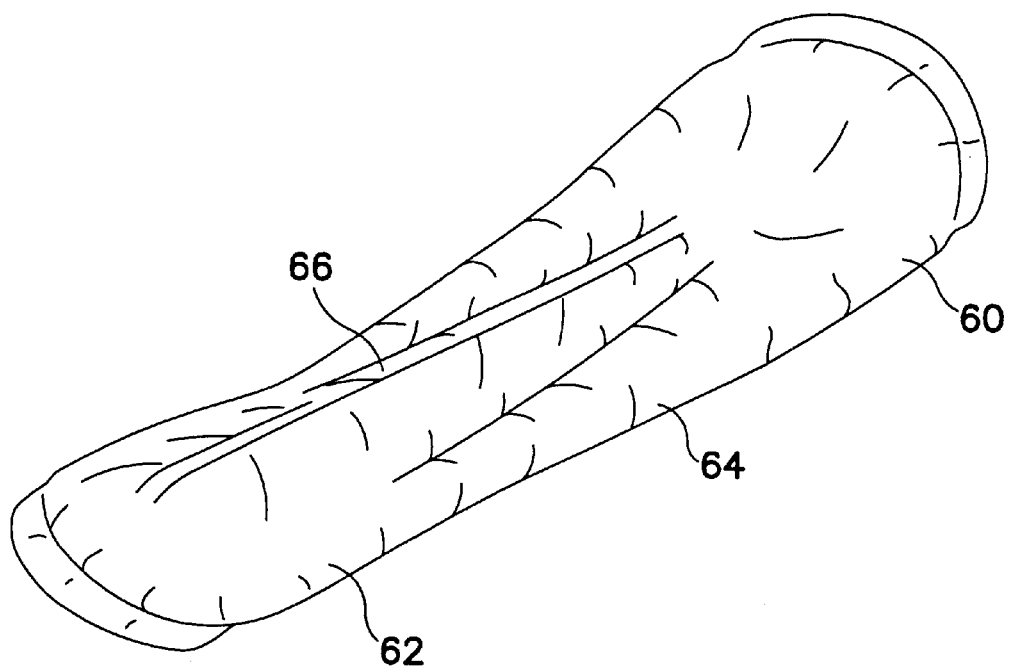
FIG. 7 is a perspective view of an absorbent article showing another body-accommodating configuration, referred to herein as the "used pad" shape, the absorbent core can obtain when lateral compressional forces are exerted on the absorbent core.

Referring to FIGS. 2 and 7, the absorbent core 18 allows the sanitary napkin 10' to assume another configuration described herein as a "used pad" shape. The shape of the anterior region 60 and the posterior region 62 are similar to that described above for the "W" shape. However, the central region 64 adopts a different shape. In this configuration, the lateral compressive forces cause the first and second members 26 and 28 to bend upwardly along the central, longitudinal flexure axis 24 toward the body of the wearer to form a convex configuration having an apex 66. The third and fourth absorbent members 38 and 40, however, remain substantially flat.

Figure 8:
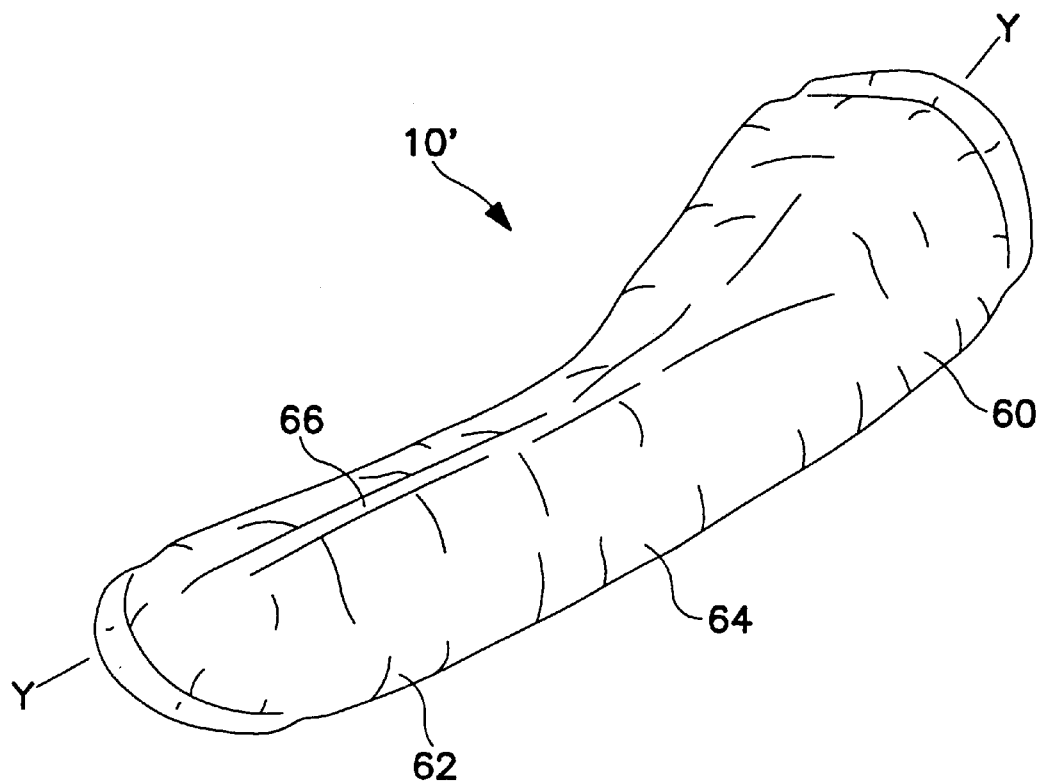
FIG. 8 is a perspective view of an absorbent article showing another body-accommodating configuration, referred to herein as the "A" shape, the absorbent core can obtain when lateral compressional forces are exerted on the absorbent core.

Referring to FIGS. 2 and 8, the absorbent core 18 allows the sanitary napkin 10' to assume another configuration described herein as an "A" shape. The central region 64 and the posterior region 62 of the sanitary napkin adapt to the gluteal groove of the wearer by bending, as viewed from the central region 64 to the posterior region 62, along the central, longitudinal flexure axis 24, upwardly toward the body-facing surface, forming an inverted "V" configuration and having an apex 66. The apex 66 of the convexly shaped body-facing surface remains the apex 66 into the posterior region 62. The apex 66 of the posterior region adapts to fit the gluteal groove of the wearer when worn. The apex 66 is generally symmetrically located between the outer periphery 16 of the sanitary napkin 10' and along the longitudinal center-line Y-Y.

The garment-facing surface 22 of the first and second members 26 and 28 of the absorbent core 18 is secured to the baffle 14 by construction adhesive (not shown) generally well known to those of ordinary skill in the art. In securing the absorbent core 18 to the baffle, it is important that the region of the central, longitudinal flexure axis 24 remain flexible compared to the flanking regions. Accordingly, less than about 80 percent of the garment-facing. surface 22 is secured to the baffle 14 and, preferably, less than about 50 percent is secured to the baffle 14. Other methods for securing the absorbent core 18 to the baffle 14 (e.g. ultrasonic, heat embossing, and the like) are equally acceptable provided the region of the central, longitudinal flexure axis 24 remains flexible compared to the flanking regions.

Figure 9:
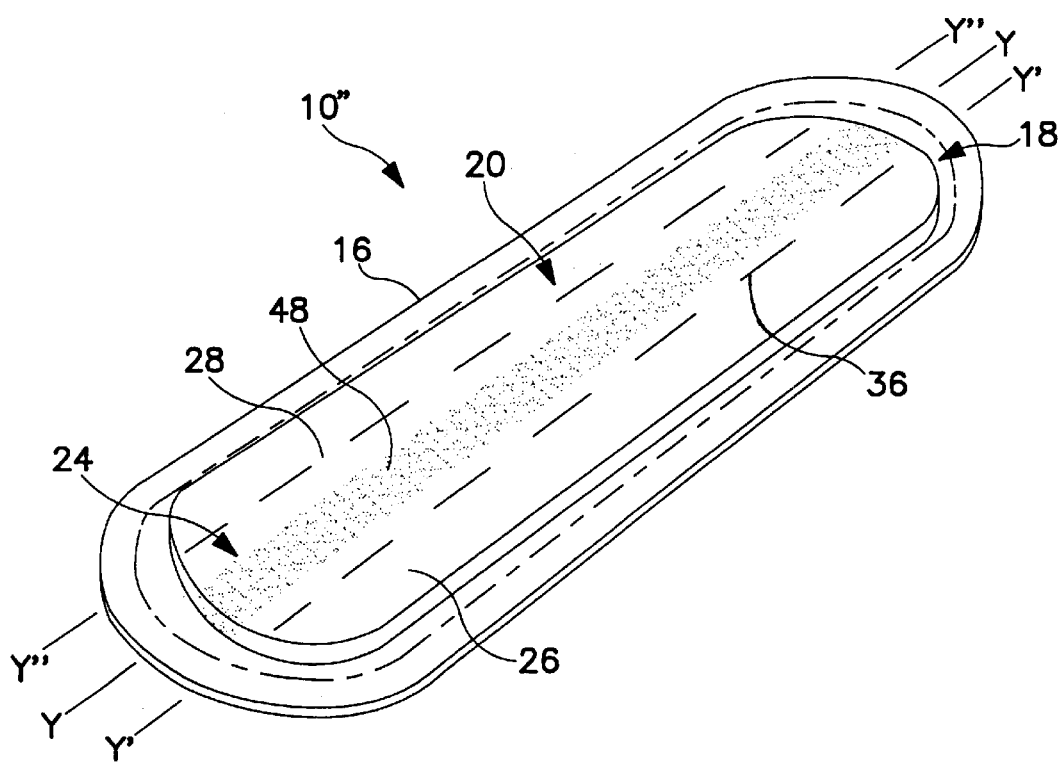
FIG. 9 is a perspective view of still another embodiment of an absorbent article having the cover removed showing an all-fluff absorbent core. The core includes a central, longitudinal flexure axis constructed of absorbent fluff having a lower density relative to the density of the flanking absorbent.

Referring to FIG. 9, another embodiment of the sanitary napkin 10" is illustrated without a cover. In this embodiment, the absorbent core 18 is constructed of an absorbent fluff well known in absorbent art. The central, longitudinal flexure axis 24 at least partially divides the absorbent core 18 into a first member 26 and a second member 28 which is similar to that described above for FIG. 1. The central, longitudinal flexure axis 24 is depicted as an area or region of low density absorbent 48. The density of the absorbent 48 should be from about 20 to about 75 percent in relation to the density of the surrounding absorbent and, preferably, is from about 30 to 50 percent. The low density absorbent 48 can include a channel or slit (not shown) similar to that discussed above for FIG. 1. The low density absorbent 48 can have a thickness substantially equal to the thickness of both the first member 26 and second member 28, but this is not required. The low density absorbent 48 is in face-to-face contact with the first and second members 26 and 28 so that body fluids contacting the low density absorbent 48 will be drawn away from the bodyside surface 20 of the absorbent core 18 and into the higher density absorbent of the first and second members 26 and 28. A higher density absorbent material may also be placed at the bottom of the central, longitudinal flexure axis 24 in order to provide a reservoir for retaining absorbed body fluid. The high density absorbent material, which may contain superabsorbents or the like, can be densified wood pulp board, a densified pulp-polyethylene mixture, polyabsorbent tissue impregnated with superabsorbent, cardboard or pulp fluff board which has been crushed to make it more flexible.

The low density absorbent 48 may be low density, loosely associated cellulose fibers, e.g. wood pulp fluff, regenerated cellulose or cotton fibers. The low density absorbent 48 can also be bicomponent fusible fibers having an outer absorbent core, which melts at relatively lower temperatures, and an inner absorbent core which melts at higher temperatures. Wood pulp is frequently the material of choice primarily because it is inexpensive and readily available.

Figure 10:
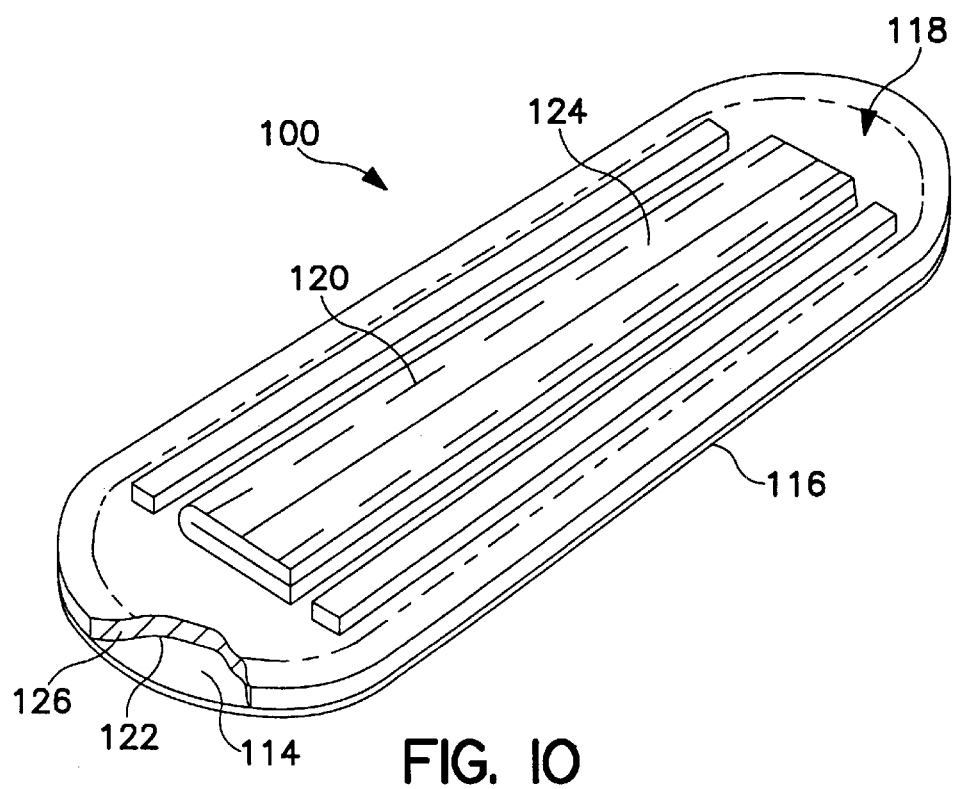
FIG. 10 is a partial cut-away perspective view of another embodiment of an absorbent article with the cover removed showing an absorbent core having a primary absorbent, similar to that illustrated in FIG. 2, and a secondary absorbent layer positioned between the primary absorbent and the baffle.

Referring to FIG. 10, another embodiment of the sanitary napkin 100 is illustrated, again without a cover. The sanitary napkin 100 includes a liquid-impervious baffle 114, an outer periphery 116 and an absorbent core 118 located intermediate the cover and the baffle 114. The absorbent core 118 is positioned inward from the outer periphery 116 of the sanitary napkin 100 and includes a body-facing surface 120, positioned adjacent the cover, and a garment-facing surface 122 positioned adjacent the baffle 114. Optionally, the sanitary napkin 100 can include a transfer layer (not shown) positioned between a cover and the absorbent core 118 for rapidly transporting body fluids into the absorbent core 118 and to reduce the occurrence of rewet.

The absorbent core 118 includes a primary absorbent 124 which is similar in function, construction and materials utilized in the absorbent core 18 described above for FIGS. 1 and 2 and includes an additional secondary absorbent layer 126 underlying the primary absorbent 124. The secondary absorbent layer 126 is positioned between the primary absorbent 124 and a liquid-impermeable baffle 114. The secondary absorbent layer 126 has an absorbent capacity which is adapted to assist the primary absorbent 124 in retaining body fluids insulting the sanitary napkin 100. Suitable absorbents that can be used in constructing the secondary absorbent layer 126, in addition to the above-described absorbent materials, includes a coform absorbent having a basis weight ranging from about 90 gsm to about 250 gsm. Coform is an air-formed combination of melt-blown polymers, such as polypropylene, and absorbent fibers, such as cellulose. The secondary absorbent layer 126 is depicted as having a free edge coterminous with the outer periphery 116 of the sanitary napkin 100, but can be located inward from the outer periphery 116 to prevent migration of the body fluid to the other periphery 116 which could possibly cause the sanitary napkin to leak. During use, the primary absorbent 124, secondary absorbent 126, baffle 114 and the cover function cooperatively to acquire any one or more of the aforementioned configurations but, preferably, will adapt to form a "W" shaped configuration in the area where lateral compressive forces are exerted on the absorbent core 118.

Figure 11:
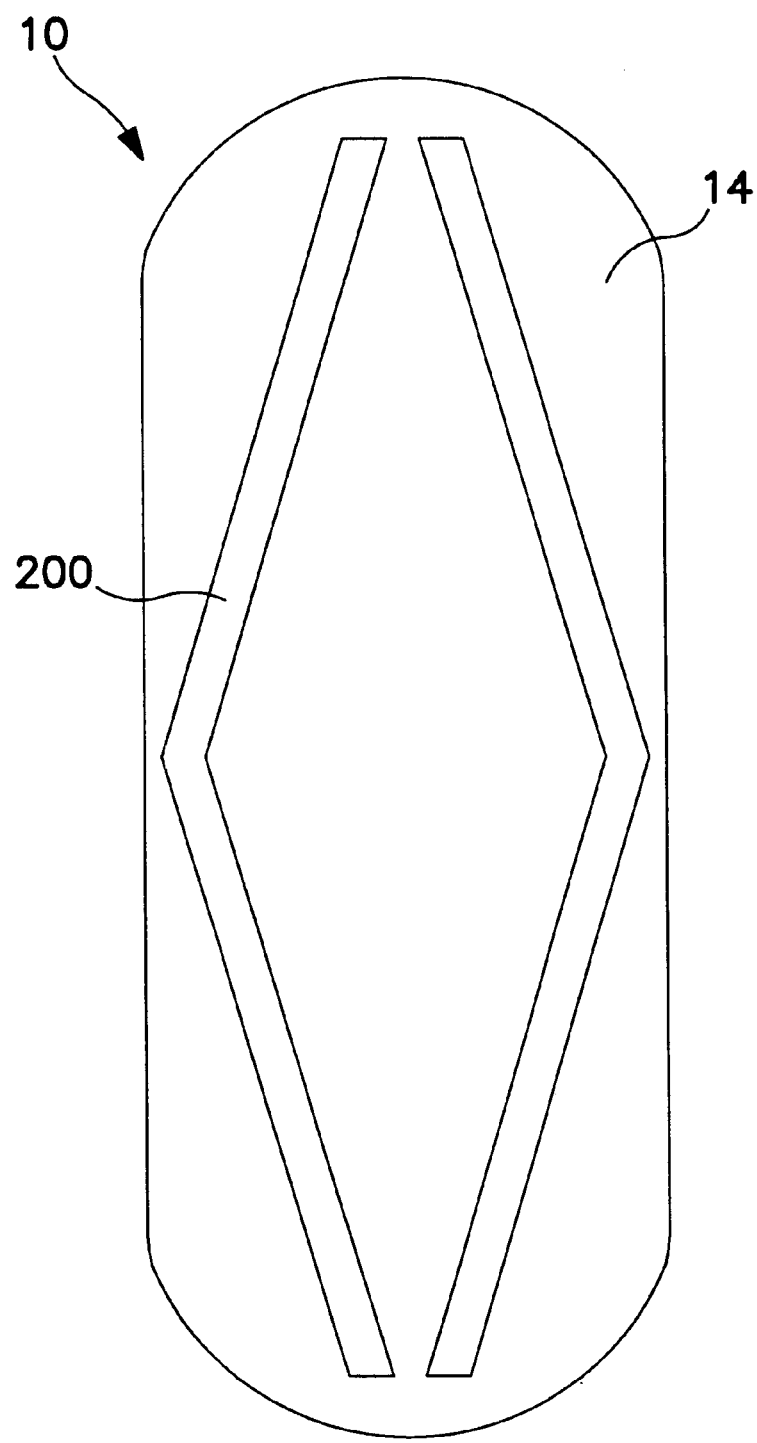
FIG. 11 is a bottom plan view of the garment side of the absorbent article showing a pattern of adhesive for securing the absorbent article to an undergarment.

Referring to FIG. 11, the garment side of the baffle 14 may further comprise a means for attaching the sanitary napkin 10 to an undergarment. Pressure sensitive adhesive 200 has commonly been found to work well for this purpose. An adhesive pattern substantially in the form of a diamond pattern is preferred, because it allows the absorbent core 18 to conform to the lateral compression forces exerted on the sanitary napkin 10. Securement to the wearer's undergarment may also be effected by utilizing a material having a sufficiently high coefficient of friction placed on the garment side of the baffle 14 (not shown) or a combination of adhesive and frictional means. Typically, the adhesive 200 is covered by a removable peel strip (not shown) to protect the adhesive prior to use of the sanitary napkin 10. Materials which can be used as a peel strip are well known to those of ordinary skill in the disposable absorbent article art.

The sanitary napkin 10 or 10' typically has a length ranging from about 18 centimeters (cm) to about 27 cm and has a width ranging from about 2 cm to about 10 cm. The sanitary napkin 10 or 10' has a caliper greater than about 4 millimeters and preferably greater than about 6 millimeters. The caliper is measured according to the following procedure.

A comparator gauge, and specifically the Ames, Model 130 with dial indicator Model 482, or equivalent, available from the B. C. Ames Company of Waltham, Mass. is needed. The comparator gauge should have a circular comparator foot made of aluminum and having a weight of 10.0 grams and a contact surface of 5.16 square centimeters. The comparator gauge is zeroed. An 80.0 grams stainless steel weight is placed on the spindle extending above the comparator dial. The comparator foot is raised and the napkin, with any panty adhesive release paper being removed, is placed garment-surface down on the base plate. The napkin is positioned on the base plate so that, when the foot is lowered, it is in the center of the napkin. Try to smooth out or avoid any wrinkles in the napkin. Gently lower the foot onto the napkin. Determine the napkin caliper by reading the comparator dial 30 seconds after the foot comes in contact with the napkin. Repeat the measurement 3.0 centimeters from each of the ends of the absorbent material along the longitudinal centerline 58 of the napkin. The average of the three readings is the caliper of the sanitary napkin.

Accordingly, there has been described an absorbent article which conforms to the contour of the wearer in the areas of the vulva, perineum, and buttocks and which provides an increased amount of absorptive surface area, which is recessed from the wearer's skin, for rapid transport of body fluids into the absorbent core.

While the invention has been described in conjunction with several specific embodiments, it is to be understood that many alternatives, modifications and variations will be apparent to those skilled in the art in light of the foregoing description. Accordingly, this invention is intended to embrace all such alternatives, modifications and variations which fall within the spirit and scope of the appended claims.

We claim:

1. An absorbent article oriented along X-, Y-, and Z-axes, said absorbent article comprising:
   (a) a liquid-permeable cover,
   (b) a liquid-impermeable baffle;
   (c) an absorbent core having a length and a thickness and being positioned between said cover and said baffle, wherein said absorbent core includes a first flexure axis which extends longitudinally through a central portion of said absorbent core along the Y-axis;
   (d) a channel extending along the first flexure axis, along the length of said absorbent core, and extending through at least about 3% up to no more than 99% of the thickness of said absorbent core, and wherein said channel forms a pocket for receiving body fluids in a direction of the Z-axis of said absorbent article to facilitate rapid absorption of such body fluids;
   (e) said absorbent core comprising first and second portions thereof extending laterally from the first flexure axis, along the X-axis, wherein each of said first and second portions has a longitudinally-extending outer boundary, said first portion having a second flexure axis which extends longitudinally along said absorbent core, said second portion having a third flexure axis which extends longitudinally along said absorbent core, the second and third flexure axes being spaced from the first flexure axis; and
   (f) in combination, a plurality of longitudinally spaced slits extending along the second and third flexure axes, and uncut portions of said absorbent core between respective ones of said slits, wherein ones of said slits on the second flexure axis are spaced from adjacent slits on the second flexure axis by distances of about 5 millimeters to about 35 millimeters whereby said first and second portions of said absorbent core comprise unslit regions thereof which extend from the first flexure axis to respective said longitudinally-extending outer boundaries of said first and second portions, and wherein, when said absorbent core is subjected to lateral compressive forces, said first and second portions preferentially bend convexly upwardly toward said cover, at the first flexure axis.

2. An absorbent article as in claim 1 wherein, when said absorbent core is subjected to lateral compressive forces, said first and second portions preferentially bend convexly upwardly toward said cover at the first flexure axis, downwardly between the first flexure axis and the second and third flexure axes, and upwardly between the second and third flexure axes and the respective longitudinally-extending outer boundaries of said absorbent core.

3. An absorbent article as in claim 1 wherein said absorbent core further includes second and third distinct absorbent members oriented longitudinally of said absorbent article along the Y-axis and positioned laterally adjacent, but spaced from, respective ones of said longitudinally-extending outer boundaries of said first and second portions of said absorbent core, said second and third members each having an inner surface laterally adjacent, and spaced from, a respective said longitudinally-extending outer boundary of a respective said first or second portion, respectively, by a distance of about 3 millimeters to about 25 millimeters.

4. An absorbent article as in claim 3 wherein said second and third members have corresponding first and second thicknesses and wherein said second and third members are spaced from respective said longitudinally-extending outer boundaries of said first and second portions by distances at least equal to the respective first or second thickness of the respective one of said second and third members.

5. An absorbent article as in claim 3 wherein, when said absorbent core is subjected to lateral compressive forces during use of said absorbent article, said absorbent core preferentially bends upwardly at the first flexure axis.

6. An absorbent article as in claim 5 wherein said absorbent core preferentially bends downwardly away from the first flexure axis, whereby said absorbent core is characterized by a W-shaped configuration.

7. An absorbent article as in claim 5 wherein said absorbent core preferentially bends downwardly away from the first flexure axis, said absorbent core being characterized by W-shaped anterior and posterior regions, and a central region having said first and second portions bent upwardly along said first flexure axis toward a body of a wearer to form a convex configuration having an apex and wherein said second and third absorbent members remain substantially flat.

8. An absorbent article as in claim 1 wherein said absorbent core further includes second and third distinct absorbent members oriented longitudinally of said absorbent article along the Y-axis, said second and third members each having an inner surface laterally adjacent, and spaced from, a respective said longitudinally-extending outer boundary of a respective said first or second portion, respectively, by a distance of about 3 millimeters to about 25 millimeters.

9. An absorbent article as in claim 1, further including a second absorbent layer positioned between said absorbent core and said baffle.

10. An absorbent article as in claim 1 wherein said plurality of slits along the second and third flexure axes are spaced laterally from the first flexure axis by a distance of about 5 millimeters to about 25 millimeters.

11. An absorbent article as in claim 1 wherein said absorbent core has a central region and a posterior region, and wherein, when said absorbent article is subjected to lateral compressive forces, said central region preferentially bends upwardly toward said cover forming an inverted V-shaped configuration having an apex, said apex being adapted to fit a gluteal groove of a wearer.

12. An absorbent article as in claim 1, further comprising a transfer layer positioned intermediate said cover and said absorbent core.

13. An absorbent core having a body-facing surface, a predetermined length, and a predetermined thickness, said absorbent core having imaginary X-, Y-, and Z-axes, and comprising:

(a) a first flexure axis extending along the Y-axis and extending longitudinally through a central portion of said absorbent core;

(b) a channel extending along the first flexure axis, along the length of said absorbent core, and extending through at least about 3% up to no more than 99% of the thickness of said absorbent core, and wherein said channel forms a pocket for receiving body fluids in a direction of the Z-axis of said absorbent article to facilitate rapid absorption of such body fluids; and (c) said absorbent core comprising first and second portions thereof extending laterally from the first flexure axis, along the X-axis, wherein each of said first and second portions has a longitudinally-extending outer boundary, said first portion having a second flexure axis, said second portion having a third flexure axis, the second and third flexure axes each including a line defining a plurality of longitudinally spaced slits in combination with uncut portions of said absorbent core between respective ones of the slits, ones of said slits along said second flexure axis being spaced from adjacent slits on the second flexure axis along a length of said second flexure axis, by distances of about 5 millimeters to about 35 millimeters whereby said first and second portions of said absorbent core comprise unslit regions thereof which extend from the first flexure axis to respective said longitudinally-extending outer boundaries of said first and second portions, and wherein, when said absorbent core is subjected to lateral compressive forces, said absorbent core generally acquires a generally W-shaped configuration.

14. An absorbent core as in claim 13 wherein said plurality of slits are spaced laterally from said first flexure axis by distances of about 5 millimeters to about 25 millimeters.

15. An absorbent core as in claim 13 wherein said slits extend through at least about 75 percent of respective said first and second portions.

16. An absorbent core as in claim 13 wherein said channel defines a pocket extending in a direction along the Z-axis to receive body fluids.

17. An absorbent core as in claim 16 wherein said pocket has an U-shaped configuration.

18. An absorbent article oriented along X-, Y-, and Z-axes, said absorbent article comprising:

(a) a liquid-permeable cover, (b) a liquid-impermeable baffle; and (c) an absorbent core having a length and a thickness, and being positioned between said cover and said baffle, wherein said absorbent core includes a first flexure axis which extends longitudinally through a central portion of said absorbent core along the Y-axis;

(d) a channel extending along the first flexure axis, whereby said channel extends along the length of said absorbent core, and extends through about 3% up to no more than 99% of the thickness of said absorbent core, and wherein said channel forms a pocket for receiving body fluids in a direction of the Z-axis of said absorbent article to facilitate rapid absorption of such body fluids;

(e) said absorbent core comprising first and second portions thereof extending laterally from the first flexure axis, along the X-axis, wherein each of said first and second portions has a longitudinally-extending outer boundary, said first portion having a second flexure axis which extends in a direction corresponding to the Y-axis, said second portion having a third flexure axis which extends in a direction corresponding to the Y-axis, the second and third flexure axes being spaced from the first flexure axis; and (f) second and third distinct absorbent members laterally spaced from respective said longitudinally-extending outer boundaries of said first and second portions while said article is at rest, by a distance ranging from about 3 millimeters to about 25 millimeters such that, when said absorbent core is subjected to lateral compressive forces, said first and second portions preferentially bend convexly upwardly about the first flexure axis.

19. An absorbent article as in claim 18 wherein said longitudinally-extending outer boundaries of said first and second portions are spaced from said second and third members, respectively, by distances at least substantially equal to the thickness of said absorbent core.

20. An absorbent article as in claim 18 wherein the second flexure axis includes a plurality of longitudinally spaced slits.

21. An absorbent article as in claim 20 wherein said slits along the second flexure axis are spaced from adjacent such slits along a length of the second flexure axis by distances of about 5 millimeters to about 35 millimeters.

* * * * *